United States Patent
Miki et al.

(10) Patent No.: US 8,091,427 B2
(45) Date of Patent: Jan. 10, 2012

(54) NONDESTRUCTIVE INSPECTION APPARATUS AND NONDESTRUCTIVE INSPECTION METHOD USING GUIDED WAVE

(75) Inventors: Masahiro Miki, Tokai (JP); Yoshiaki Nagashima, Hitachi (JP); Masao Endou, Kitaibaraki (JP); Kojiro Kodaira, Hitachinaka (JP); Mitsuru Odakura, Hitachi (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 481 days.

(21) Appl. No.: 12/176,671

(22) Filed: Jul. 21, 2008

(65) Prior Publication Data

US 2009/0031813 A1 Feb. 5, 2009

(30) Foreign Application Priority Data

Jul. 31, 2007 (JP) ................................. 2007-198283

(51) Int. Cl.
*G01N 29/04* (2006.01)
(52) U.S. Cl. ........................................... 73/622; 73/602
(58) Field of Classification Search .................... 73/622, 73/602, 612, 620, 627
See application file for complete search history.

(56) References Cited

U.S. PATENT DOCUMENTS

| | | | | |
|---|---|---|---|---|
| 6,581,014 B2 * | 6/2003 | Sills et al. | ........................ | 702/39 |
| 6,597,997 B2 * | 7/2003 | Tingley | ............................ | 702/34 |
| 6,751,560 B1 * | 6/2004 | Tingley et al. | ................... | 702/51 |
| 6,799,466 B2 * | 10/2004 | Chinn | .............................. | 73/622 |
| 6,917,196 B2 * | 7/2005 | Kwun et al. | ................... | 324/240 |
| 6,923,067 B2 * | 8/2005 | Coen et al. | ....................... | 73/627 |
| 6,925,881 B1 * | 8/2005 | Kwun et al. | ................... | 73/600 |
| 7,017,422 B2 * | 3/2006 | Heyman et al. | ................... | 73/827 |
| 7,171,854 B2 | 2/2007 | Nagashima et al. | | |
| 7,417,444 B2 * | 8/2008 | Shinada et al. | ........... | 324/754.22 |
| 7,565,252 B2 * | 7/2009 | Kim et al. | ........................ | 702/35 |
| 7,573,261 B1 * | 8/2009 | Vinogradov | ................... | 324/240 |
| 7,634,392 B2 * | 12/2009 | Kwun et al. | ....................... | 703/5 |

FOREIGN PATENT DOCUMENTS

| | | |
|---|---|---|
| JP | 2002-131296 A | 5/2002 |
| JP | 2003-232779 A | 8/2003 |
| JP | 2004-085370 | 3/2004 |
| JP | 2004-301540 | 10/2004 |
| JP | 3747921 | 12/2005 |
| JP | 2006-170754 A | 6/2006 |

(Continued)

OTHER PUBLICATIONS

"Discontinuity-Length Sizing Potential Using Ultrasonic Guided Waves in Pipes" Y. Nagashima, et al., 15th International Conference on Nuclear Engineering, 2007.

(Continued)

*Primary Examiner* — J M Saint Surin
(74) *Attorney, Agent, or Firm* — Mattingly & Malur, P.C.

(57) ABSTRACT

Disclosed herein are an apparatus and a technique for quickly detecting a defective portion including wastage, which has occurred in piping having a straight piping portion or a bending zone, in the nondestructive inspection using a guided wave. A guided wave sensor 3 included in a guided wave inspection device 4 is mounted to the outer surface of piping 1. A guided wave is propagated to an inspection area of the piping 1. If a defective portion exists, the guided wave sensor 3 receives the guided wave that has been reflected from the defective portion. As a result, the guided wave inspection device 4 can acquire receive information including receive information derived from the defect.

10 Claims, 12 Drawing Sheets

FOREIGN PATENT DOCUMENTS

JP        2007-003469        1/2007

OTHER PUBLICATIONS

"A Pulse/Echo Technique with Compensating Dispersion Effect of Ultrasonic Guided Waves" by Y. Nagashima, et al., 2006.

Yoshiaki Nagashima et al., Development of Pipe Wall Thinning Inspection Technique for Power Plant Using Ultrasonic Guided Wave, Steam Nuclear Power Generation, Nov. 2006, pp. 38-43, vol. 57, No. 603.

* cited by examiner

NONDESTRUCTIVE INSPECTION APPARATUS AND NONDESTRUCTIVE INSPECTION METHOD USING GUIDED WAVE

BACKGROUND OF THE INVENTION

1. Field of the Invention

The present invention relates to a technical field in which nondestructive inspection is performed in piping including a pipe by use of a guided wave so as to collectively evaluate, over long distance, a defect such as wastage that is assumed to occur in a material.

2. Description of the Related Art

Piping used in a power plant, a chemical plant, or the like may be subjected to corrosion and erosion on its inner surface due to the influence of liquid or gas flowing through the piping during the long-term operation of the plant. As a result, deterioration of the piping is promoted in some cases and what is worse, a hole may be disadvantageously bored in the piping in the thickness-wise direction thereof. In such a case, fluid inside the piping such as liquid or vapor leaks and thereby normal operation of the plant will not be performed. As a result, the plant is obliged to stop the operation thereof for a long time. For this reason, it is necessary to evaluate the thickness of piping and a state of material using a nondestructive inspection technique, and then to take measures including the replacement or repair of the piping before the leakage occurs.

One of typical examples of the above-described nondestructive inspection technique is a thickness measurement method using an ultrasonic thickness gauge, which is specified in JIS Z 2355. The thickness measurement method using the ultrasonic thickness gauge is a method for measuring the thickness of piping by exciting an elastic wave in a thickness direction of target piping using an ultrasonic probe, and then by receiving the elastic wave reflected from the bottom surface of the piping using the ultrasonic probe. This ultrasonic thickness gauge measures the thickness of piping by use of the ultrasonic wave propagation time based on a received wave and the known sound velocity and is capable of measuring the thickness of piping with a high degree of accuracy. However, an effective inspection range is a level of the piping contact area of a probe. If a piping diameter is large, or if an inspection range becomes wide (for example, piping whose length ranges from several meters to several tens of meters), the number of measuring points to be measured by the ultrasonic thickness gauge will increase. As a result, it disadvantageously takes much time to complete the inspection. In addition, in the case of such piping that it is difficult for an inspector and an inspection apparatus to access the piping (for example, piping covered by a heat insulator, buried piping, and vertical piping which extends to a high place), it will take much time for the preparation of inspection and clearance work after inspection.

To overcome the above-mentioned drawbacks, inspection technology using a guided wave, which can collectively inspect a long-distance wide area, has been introduced. The principles of a guided wave will be briefly described with reference to FIG. 1. A plurality of ultrasonic sensors or magnetostrictive sensors are arrayed in the circumference direction of piping 1. When the sensors are excited, a guided wave mode is generated in which a guided wave propagates through a material in the piping. Because guided waves have characteristics that the energy thereof is not easily attenuated, the wave motion propagates over long distance. In addition, when the exciting time is controlled, a wave motion mode which allows a defect to be easily detected can be transmitted. If an unevenness portion in thickness of piping is present in the propagation direction (for example, if there is a wastage portion), a guided wave propagating through a straight piping scatters a reflected wave towards the upstream side of a transmitted wave. Thus, receiving the scattered reflected wave makes it possible to detect a defect.

The conventional inspection method that uses a guided wave is described in JP-A-2004-301540. According to this method, a guided wave transmission technique is used to measure the depth of wastage of piping, and the inspection result obtained is then displayed as an image for its evaluation.

SUMMARY OF THE INVENTION

The nondestructive inspection method using a guided wave has an advantage that because long-distance collective inspection can be performed, inspection can be completed in a much shorter period of time than that in the thickness measurement method that uses an ultrasonic thickness gauge. Moreover, because the time it takes for the preparation of inspection and clearance work after inspection can be shortened, it becomes possible to shorten the total work hours including time for preparation and removal processes.

However, the nondestructive inspection method using a guided wave has a disadvantage that it is difficult to apply this inspection to a bent portion of piping. Bending a portion of piping causes a piping material to expand to some extent, resulting in uneven thickness. In addition, at a bending zone, there is a difference in effective length of piping between the inside and outside of the piping. Accordingly, when a guided wave propagating through a straight piping portion passes through the bending zone, piping deformation occurs, and part of a guided wave breaks up and is reflected to be scattered and propagated toward the upstream side of a transmitted wave. Because this makes it difficult to detect a defect, the nondestructive inspection method using a guided wave is not judged to be effective.

Therefore, when a bending zone of piping is to be inspected, the thickness measurement using the ultrasonic thickness gauge described above is obliged to be performed.

Therefore, an object of the present invention is to provide an apparatus and a technique for quickly detecting a defect including wastage, which has occurred in piping, in the nondestructive inspection using a guided wave irrespective of whether a target to be inspected is a bending zone or a straight piping portion.

In order to achieve the object of the present invention, in one aspect, there is provided a nondestructive inspection apparatus comprising: a guided wave inspection device for propagating a guided wave into a piping, and for receiving the guided wave from the piping to acquire receive information based on the received guided wave; an inspection waveform storage device for storing the receive information; and an inspection-result diagnostic device for, on the basis of the receive information stored in the storage device and predetermined reference receive information, performing arithmetic processing of extracting receive information associated with a defect that may occur in the piping.

Preferably, the inspection waveform storage device stores the receive information and estimated receive information which is estimated when a guided wave propagating through the piping is received, the piping being free from a defect to be detected, and the inspection-result diagnostic device performs arithmetic processing of extracting receive information associated with a defect on the basis of the estimated receive information and the receive information which are stored in the storage device.

Preferably, the inspection waveform storage device includes an operation processing unit for calculating propagation behavior of a guided wave propagating through the piping free from a defect to be detected to generate the estimated receive information.

Preferably, the inspection-result diagnostic device includes an operation processing unit for calculating the difference in the receiving time between the receive information and the reference receive information or between the receive information and the estimated receive information, so as to extract receive information associated with a defect.

In another aspect, there is provided a nondestructive inspection apparatus comprising: a pair of guided wave inspection devices disposed on an outer surface of piping, each of the devices being capable of exciting an elastic wave into a piping to propagate a guided wave, and each of the devices being capable of receiving the guided wave propagating through the piping; an inspection-result storage device for storing the guided wave received by the guided wave inspection device as a digitized signal of the received wave; means for transmitting, as a transmission signal, a waveform obtained by time-reversing a waveform reproduced from the inspection-result storage device from the pair of guided wave inspection devices; and an inspection-result diagnostic device for, on the basis of a signal of each received wave acquired by transmitting/receiving a guided wave based on the time-reversed waveform into/from the piping by use of the pair of guided wave inspection devices, performing arithmetic processing of judging whether or not a signal associated with a defect exists.

In a still another aspect, there is provided a nondestructive inspection method comprising the steps of: disposing a pair of means A and B, each of which is capable of generating and receiving a guided wave, in such a manner that a range of piping to be inspected is put between the pair of means A, B; receiving the guided wave generated by one means A by the other means B, allowing the means B to transmit the guided wave which has been subjected to waveform control by time-reversing on the basis of the received wave to the range of piping to be inspected, and handling a waveform received by the means B as a received signal 1; receiving a guided wave generated by the means B by the means A, allowing the means A to transmit the guided wave which has been subjected to waveform control by time-reversing on the basis of the received wave to the range of piping to be inspected, and handling a waveform received by the means A as a received signal 2; and identifying a signal derived from a defect by calculating the sum and difference of the receiving time between the received signal 1 and the received signal 2.

According to the present invention, it is possible to quickly detect a defect by an inspection using a guided wave over a wide inspection area including not only a straight piping portion of a piping but also a bending zone whose thickness is obliged to be measured by an ultrasonic thickness gauge.

DESCRIPTION OF THE PREFERRED EMBODIMENTS

Figure 1:
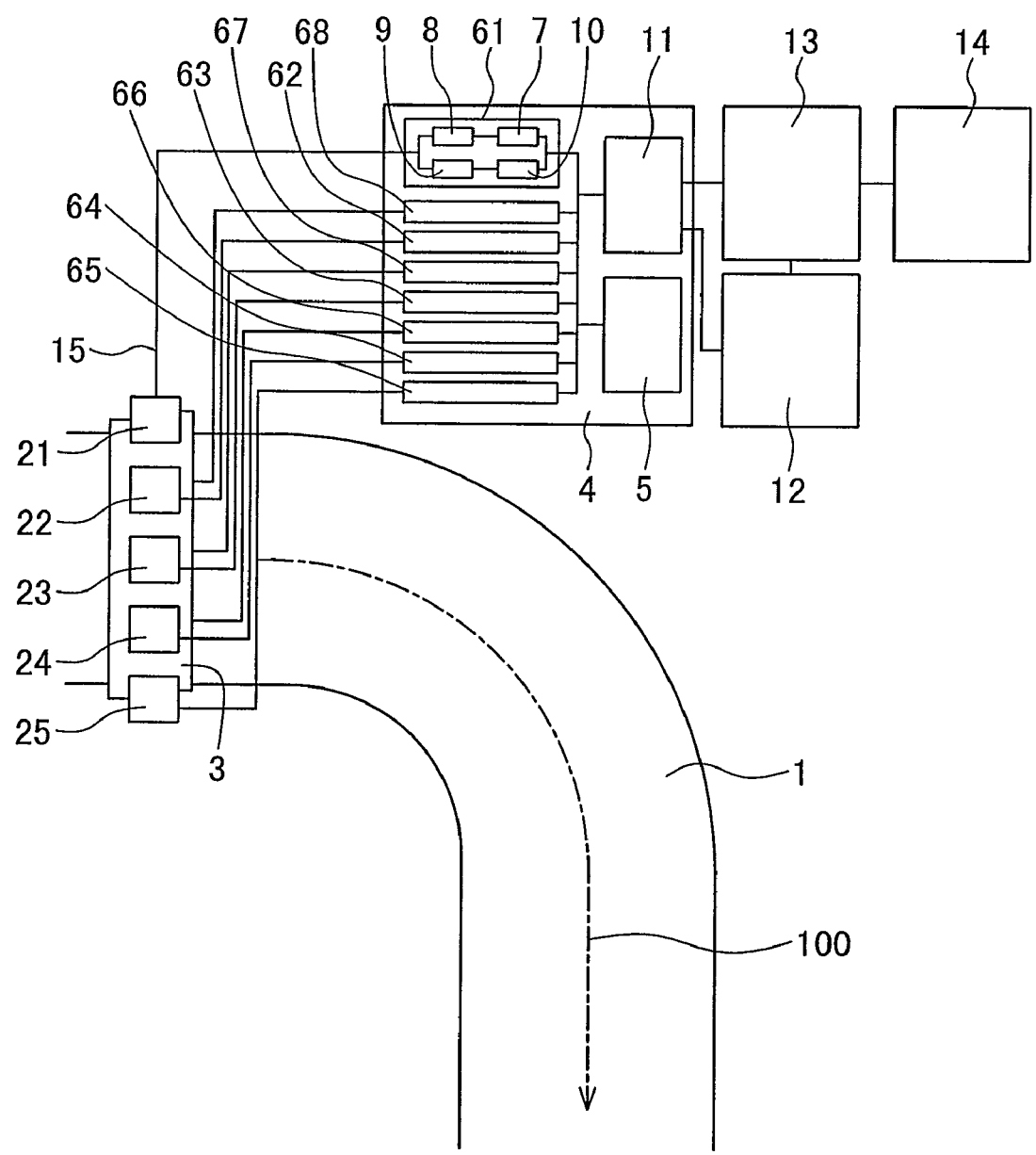
FIG. 1 is an overall view illustrating a nondestructive inspection apparatus according to a first embodiment of the present invention.
Figure 2:
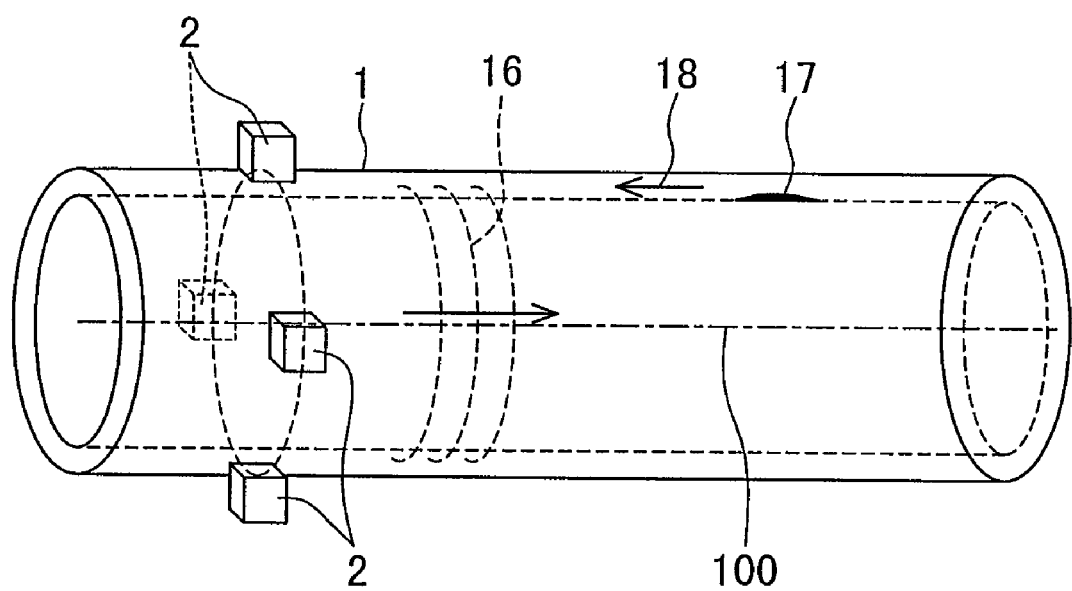
FIG. 2 is a diagram illustrating a guided wave inspection method that is generally used.

Embodiments of the present invention will be described with reference to the drawings as below.

First Embodiment

A first embodiment of the present invention will be described with reference to FIGS. 1-4. A guided wave inspection device 4 is a device for transmitting/receiving a guided wave into/from a piping. The guided wave inspection device 4 includes a trigger signal generator 5, a plurality of transmit-receive circuits 61 through 68, and a received waveform converter 11 as main elements.

The transmit-receive circuit 61 is connected to an ultrasonic probe 21 through an electric wire 15. Here, the transmit-receive circuits 61 through 68 have the same configuration and function so that the transmit-receive circuits 61 through 68 operate in the same manner. The ultrasonic probes 21 through 28 have the same configuration and performance so that the ultrasonic probes 21 through 28 operate in the same manner.

Hereinafter, circuits relating to the transmit-receive circuit 61 and the ultrasonic probe 21 will be described. In addition, the ultrasonic probes 21 through 28 are connected to the transmit-receive circuits 61 through 68 respectively to have one-to-one correspondence.

A trigger signal transmitted from the trigger signal generator 5 is transferred to the transmit-receive circuit 61. In response to this trigger signal, a transmission signal is transmitted from an arbitrary-waveform generator 7. An amplifier 8 amplifies the amplitude of the transmission signal. The amplified transmission signal is then transmitted to the ultrasonic probe 21.

The ultrasonic probe 21 receives the transmission signal. The ultrasonic probe 21 then transmits an elastic wave into the piping to induce a guided wave in the piping so that the guided wave is propagated. If there is unevenness such as wastage in the piping, a reflected wave towards the upstream direction (propagation origin point) of the guided wave, which is the transmitted wave, occurs. This reflected wave is received by the ultrasonic probe 21.

The amplitude of the received signal is amplified by a receive amplifier 9 of the transmit-receive circuit 61. The amplified signal is then transmitted to a digital signal converter 10. The digital signal converter 10 converts the amplified signal into a digital signal, and then transmits the converted signal to a received waveform converter 11. Next, the received waveform converter 11 performs superimposing processing of signals obtained from the ultrasonic probes 21 through 28 so that the received signal is measured and identified as a received waveform. The received signal and the received waveform subjected to the superimposing processing are handled as receive information.

The received waveform converter 11, an inspection waveform storage device 12, and a display unit 14 are connected to an inspection-result diagnostic device 13. A received waveform acquired by measuring a region to be inspected of piping using a guided wave sensor and the ultrasonic probe is stored in the inspection waveform storage device 12 as reference receive information. In this case, the region to be inspected of piping is in a pre-service or molded state based on the same process, material and standards. Accordingly, the received waveform 31a stored beforehand can be acquired from the inspection waveform storage device 12 when necessary.

Figure 3:
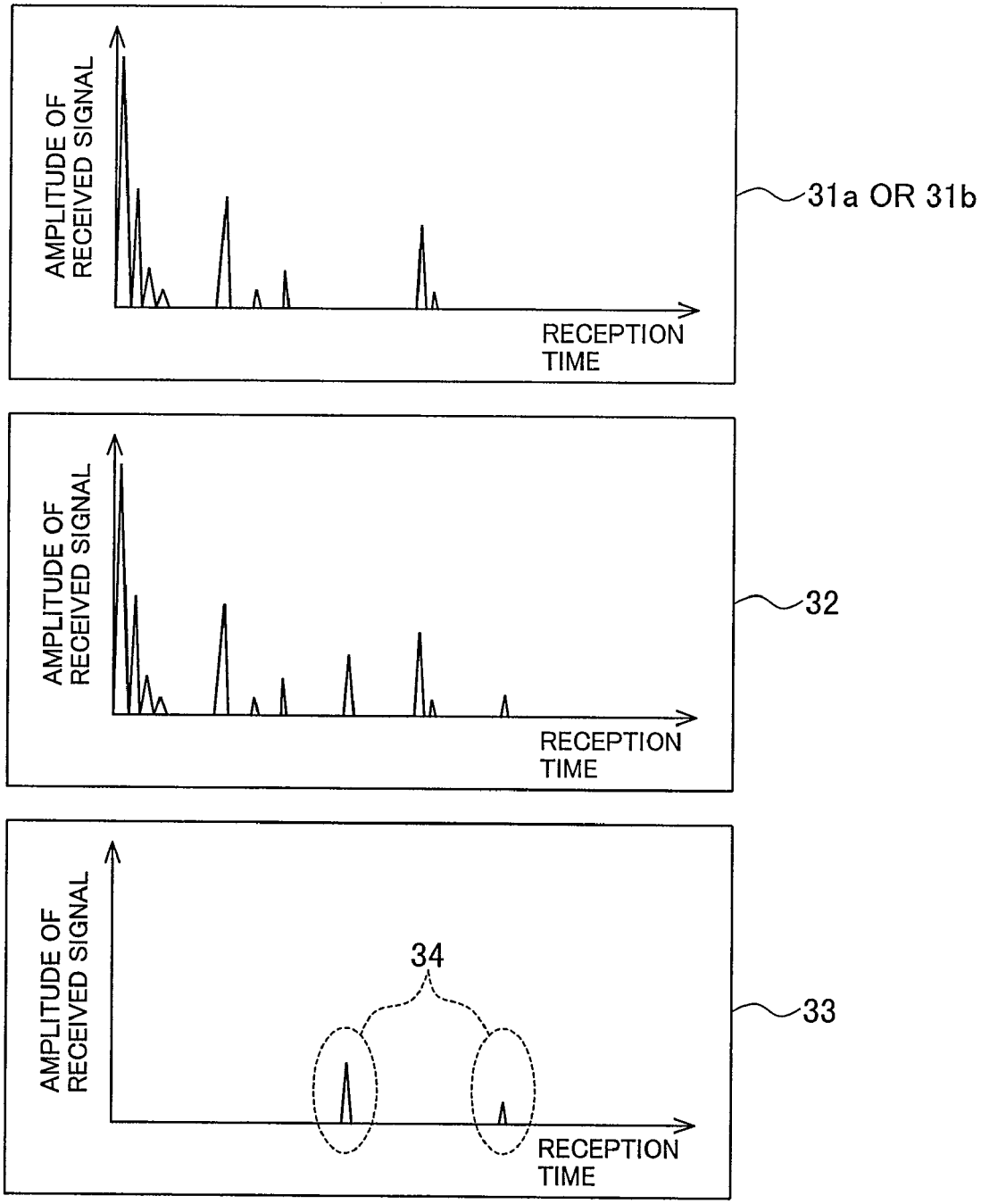
FIG. 3 shows charts each illustrating a defect identification method using a nondestructive inspection apparatus according to the first embodiment of the present invention.

As shown in FIG. 3, the inspection-result diagnostic device 13 has a function of comparing a received waveform 31a stored beforehand by the above means with a received waveform 32 acquired by the actual inspection to determine a waveform 33 that is the difference between both of the received waveforms. With the above function, if a significant signal 34 derived from a defect is detected, it is possible to judge that the signal in question is based on the defect, and thereby defect detection can be made. Waveforms shown in FIG. 3 are displayed on the display unit 14.

Figure 4:
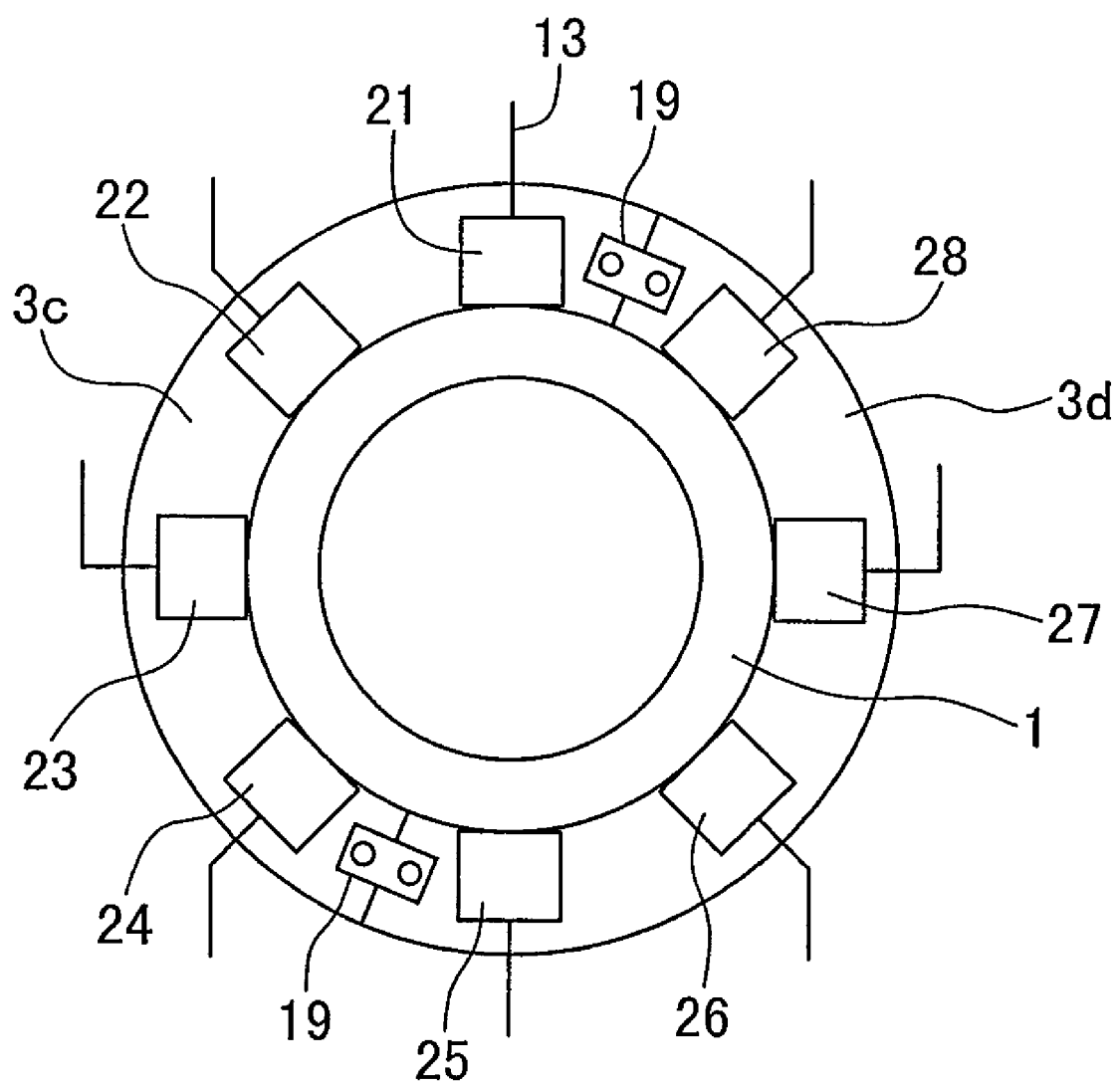
FIG. 4 is a diagram illustrating a guided wave sensor according to the first embodiment of the present invention.

A guided wave sensor 3 will be described with reference to FIG. 4 as below. The guided wave sensor 3 disposed on a straight piping portion of the piping 1 is formed of halved guided wave sensor rings 3c, 3d, and a plurality of ultrasonic probes 21 through 28. With the guided wave sensor rings 3c, 3d joined together on the outside surface of the piping, the guided wave sensor rings 3c, 3d are secured by the use of guided wave sensor fixtures 19 so that the guided wave sensor rings 3c, 3d are not displaced from the piping.

The guided wave sensor rings 3c, 3d are provided for the guided wave sensor 3 according to a piping diameter; the basic configurations thereof are the same. An elastic wave is transmitted into a material in the piping by the ultrasonic probes 21 through 28 such that a signal derived from a defect and an unevenness portion in the piping can be received.

In addition, one of the embodiments of the present invention is that the inspection waveform storage device 12 has a function of calculating a guided wave propagating through the piping. Here, when the guided wave propagating through the piping is calculated, calculation grids are automatically generated on the basis of information about a piping diameter, the thickness, and a piping shape. After that, a numerical analysis solution can be determined based on an analytical technique represented by the finite element method in which material characteristics and transmitted ultrasonic wave information are input conditions. The numerical analysis solution is obtained by solving a governing equation based on elastic theory. Thus, there is provided the function of calculating propagation behavior of a guided wave propagating through the piping. An estimated waveform 31b, which is a received waveform acquired when the piping in question has no defect, is calculated. The estimated waveform 31b is used as estimated receive information.

The inspection-result diagnostic device 13 compares this estimated waveform 31b with the waveform 32 that has been actually measured by the guided wave inspection, and thereby calculates a waveform 33 that is the difference between both of the waveforms. If a significant signal is detected, it is possible to judge that the signal is based on a defect, and thereby defect detection can be made. In addition, the estimated received waveform 31b may also be stored in the inspection waveform storage device 12 as a database.

This eliminates the need for acquiring the received waveform 31a that is stored beforehand as a result of the guided wave inspection at the time of the installation. Therefore, it becomes easy to apply the guided wave inspection to the piping inspection of existing equipment. Moreover, molding of new piping based on the same process, material, and standards, and the preliminary inspection using the new piping, are unnecessary.

Second Embodiment

Figure 5:
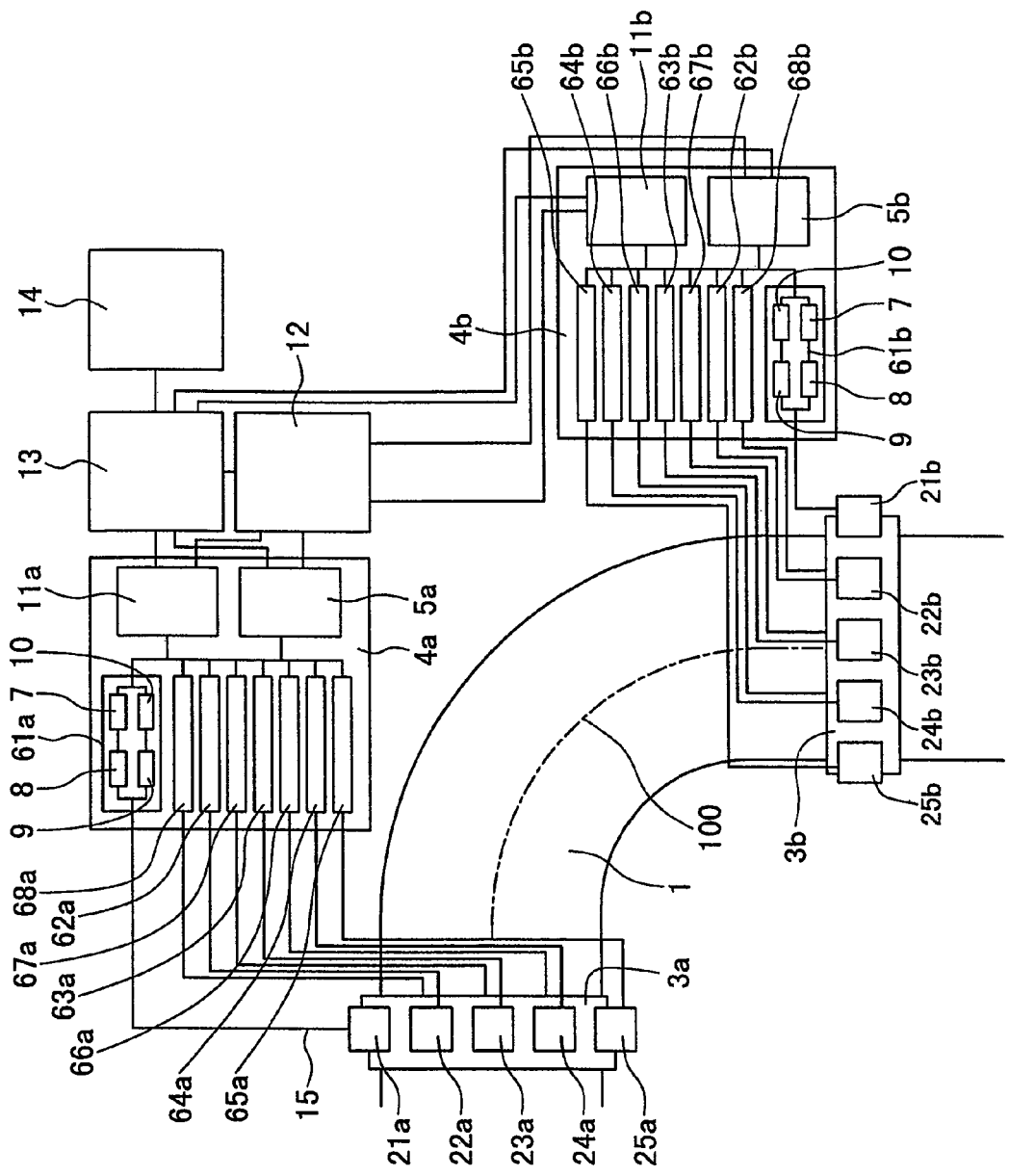
FIG. 5 is an overall view illustrating a nondestructive inspection apparatus according to a second embodiment of the present invention.

A second embodiment of the present invention will be described with reference to FIG. 5. Guided wave inspection devices 4a, 4b are devices for transmitting/receiving a guided wave into/from a piping. The guided wave inspection devices 4a, 4b have the same elements and functions, and are capable of operating in the same manner.

The guided wave inspection device 4a includes a trigger signal generator 5a, transmit-receive circuits 61a through 68a, and a received waveform converter 11a. The transmit-receive circuit 61a is connected to an ultrasonic probe 21a through an electric wire 15. Here, the transmit-receive circuits 61a through 68a have the same configuration and function so that the transmit-receive circuits 61a through 68a operate in the same manner. The ultrasonic probes 21a through 28a have the same configuration and performance, so that the ultrasonic probes 21a through 28a operate in the same manner.

Hereinafter, circuits relating to the transmit-receive circuit 61a and the ultrasonic probe 21a will be described. In addition, the ultrasonic probes 21a through 28a are connected to the transmit-receive circuits 61a through 68a respectively to have one-to-one correspondence.

In addition, the guided wave inspection device 4b includes a trigger signal generator 5b, transmit-receive circuits 61b through 68b, and a received waveform converter 11b. The transmit-receive circuit 61b is connected to an ultrasonic probe 21b through the electric wire 15. Here, the transmit-receive circuits 61b through 68b have the same configuration and functions so that the transmit-receive circuits 61b through 68b operate in the same manner. The ultrasonic probes 21b through 28b have the same configuration and performance, so that the ultrasonic probes 21b through 28b operate in the same manner. Hereinafter, circuits relating to the transmit-receive circuit 61b and the ultrasonic probe 21b will be described. In addition, the ultrasonic probes 21b through 28b are connected to the transmit-receive circuits 61b through 68b respectively for one-to-one correspondence. A pair of means A and B, each of which is capable of generating and receiving a guided wave, corresponds to the guided wave inspection devices 4a, 4b, respectively.

Guided wave sensors 3a and 3b are mounted on the outer surface of the piping in such a manner that a region to be inspected is placed between the guided wave sensors 3a, 3b. The guided wave sensors 3a, 3b are configured in the same manner as that described with reference to FIG. 4.

A trigger signal transmitted from the trigger signal generator 5a is transmitted to the transmit-receive circuit 61a. In response to this trigger signal, a transmission signal is transmitted from an arbitrary-waveform generator 7. An amplifier 8 amplifies the amplitude of the transmission signal. The amplified transmission signal is then transmitted to the ultrasonic probe 21a. The ultrasonic probe 21a receives the transmission signal. The ultrasonic probe 21a then transmits an elastic wave into the piping to induce a guided wave in the piping. If there is an unevenness portion (for example, wastage) in the piping, a reflected wave towards an upstream direction of the transmitted wave occurs.

This reflected wave is received by the ultrasonic probe 21a. The received signal is amplified by a receive amplifier 9 of the transmit-receive circuit 61a and then the amplified signal is transmitted to a digital signal converter 10. Next, the digital signal converter 10 converts the amplified signal into a digital signal. The digital signal is then transmitted to a received waveform converter 11a in which the digital signal is measured as a received waveform. The received waveform converter 11a, an inspection waveform storage device 12, and a display unit 14 are connected to an inspection-result diagnostic device 13.

Figure 6:
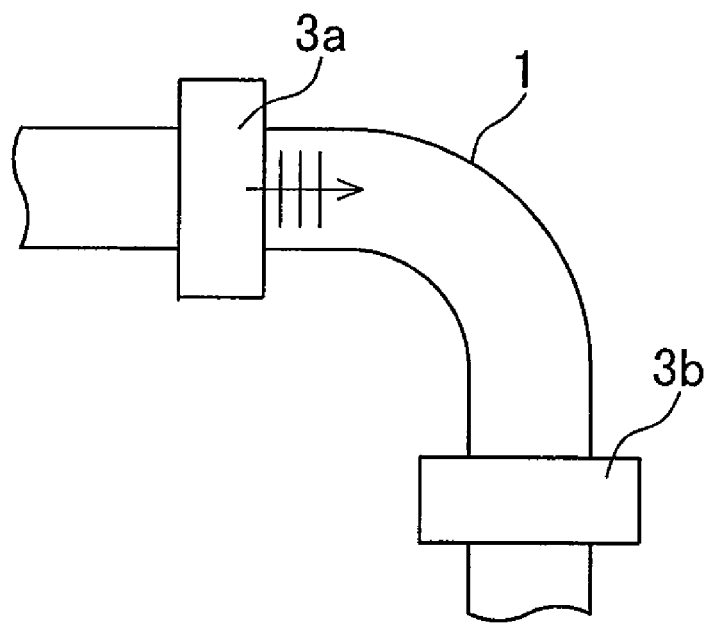
FIG. 6 is a diagram illustrating a first inspection process using a nondestructive inspection apparatus according to the second embodiment of the present invention.
Figure 16:
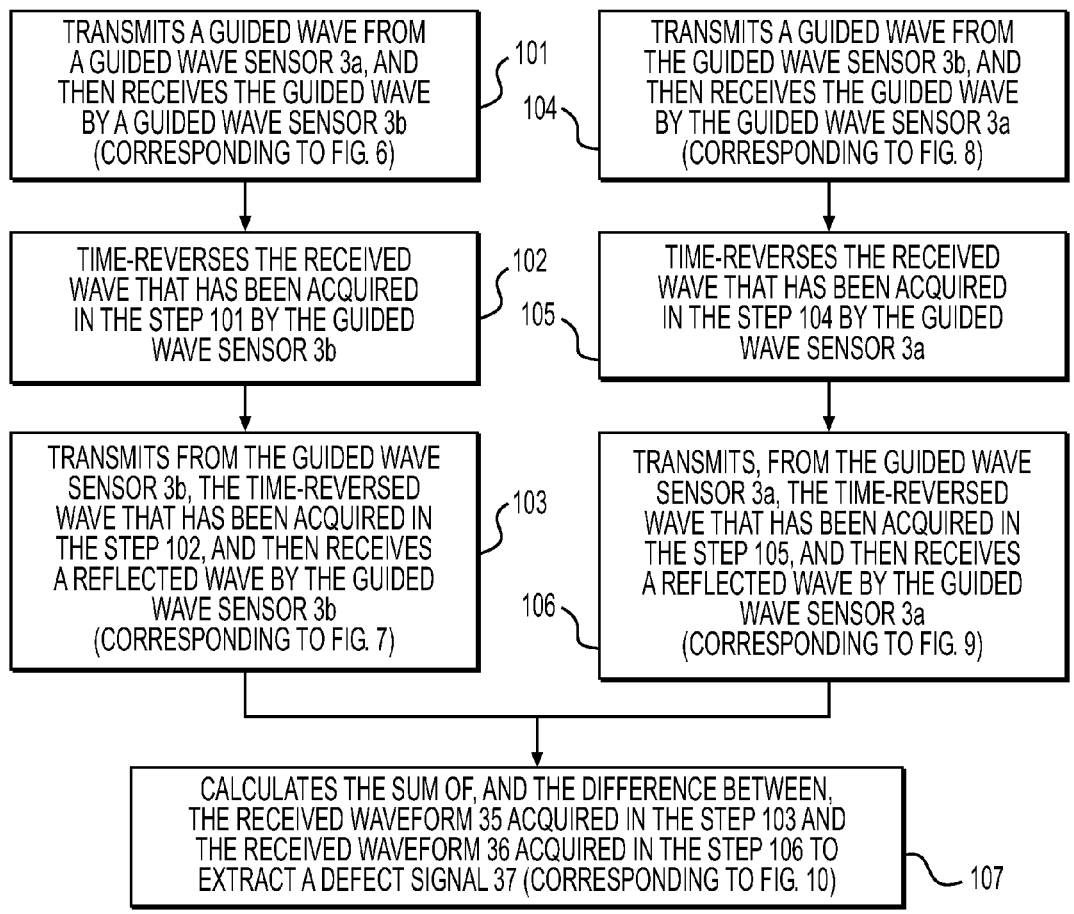
FIG. 16 is a flowchart illustrating the workflow according to the second embodiment of the present invention.

Inspection procedures according to the second embodiment will be described with reference to FIGS. 6 through 10 and FIG. 16. To begin with, processing in a step 101 shown in FIG. 16 is performed. As shown in FIG. 6, in response to a trigger signal from the trigger signal generator 5a, transmitted waves each having the same waveform are transmitted from the ultrasonic probes 21a through 25a according to the above-described operation. In this case, the phase and excitation amplitude are adjusted so that a guided wave mode which is suitable for inspection within a target range is excited.

In this way, a guided wave free from breakup is transmitted into the piping. When a guided wave propagates from a straight piping portion at which the guided wave sensor 3a is disposed to a bending zone and then passes through the bending zone, the guided wave is broken up at the bending zone. This breakup is caused by: the unevenness in thickness caused by the slight expansion that has occurred at the time of bending; and the difference in effective length of piping between the inside and outside of the bending zone. This broken-up guided wave is received by the ultrasonic probes 21b through 25b of the guided wave sensor 3b. The received signal is amplified by the receive amplifier 9 of each of the transmit-receive circuits 61b through 68b and the amplified signal is then transmitted to the digital signal converter 10. The digital signal converter 10 converts the amplified signal into a digital signal, and then transmits the digital signal to the received waveform converter 11b.

Figure 17:
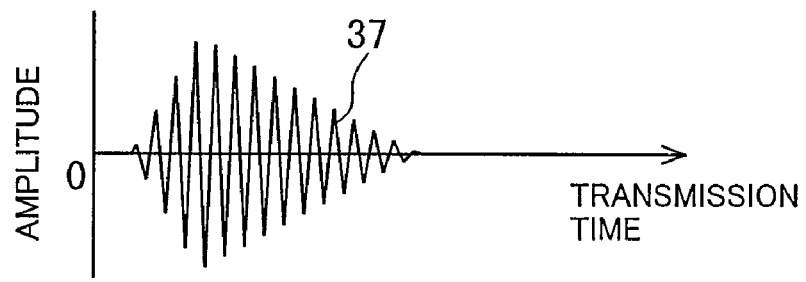
FIG. 17 shows charts each illustrating a time-reversing wave according to the second embodiment of the present invention.
Figure 17:
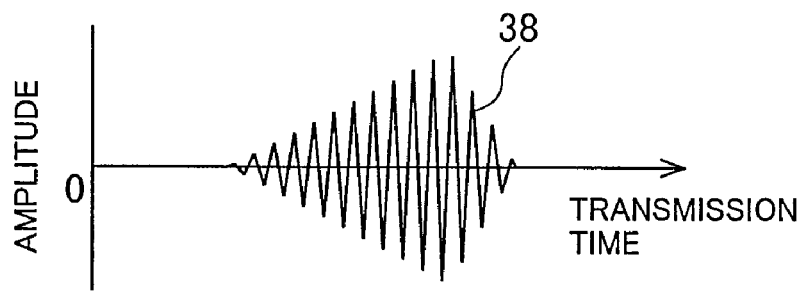

Next, processing in a step 102 shown in FIG. 16 is performed. As shown in FIG. 17, the received waveform 37 acquired by the received waveform converter 11b is transmitted to the arbitrary-waveform generator 7 as a waveform 38 whose signal is time-reversed so that a signal being received last is transmitted first. In this case, the time-reversed waveform in the ultrasonic probe 21b is adapted to be received into the arbitrary-waveform generator 7 of the transmit-receive circuit 61b. The arbitrary-waveform generators of the other transmit-receive circuits are also set according to this configuration.

Figure 7:
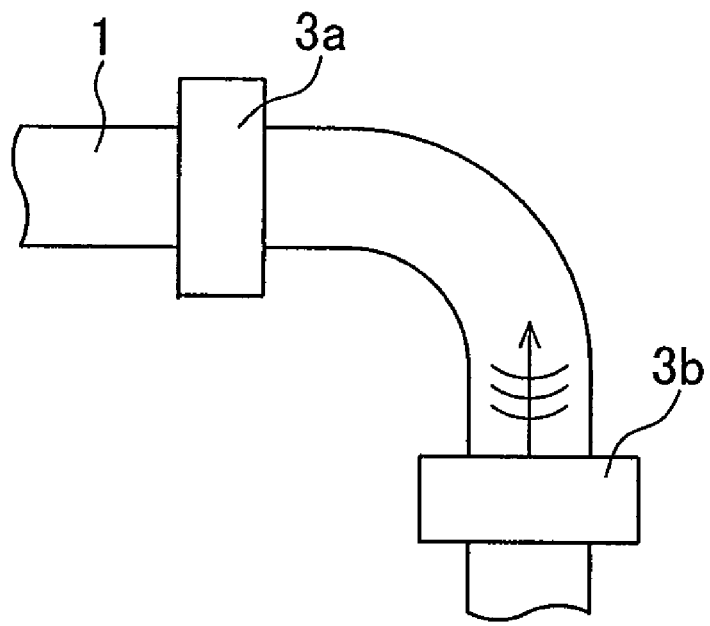
FIG. 7 is a diagram illustrating a second inspection process using a nondestructive inspection apparatus according to the second embodiment of the present invention.

In addition, processing in a step 103 shown in FIG. 16 is performed. As shown in FIG. 7, in response to a trigger signal from the trigger signal generator 5b, a time-reversed wave, which has been inputted from each of the ultrasonic probes 21b through 25b to the arbitrary-waveform generator 7, is transmitted as an in-phase transmitted wave according to the above-described operation.

When a wave having broken-up wave motion time-reversed is transmitted, the wave passing through the bending zone becomes a wave free from breakup, which is due to the reversibility of a wave motion. This enables the wave motion control in the bending zone. Inspection is carried out by use of this control transmission wave.

If a signal caused by bending or a defect such as wastage is present in a region within a range to be inspected, a reflected wave is generated from the region. The reflected wave is received by the ultrasonic probes 21b through 25b. The received signal passes through each of the transmit-receive circuits 61b through 68b, and is then transmitted to the received waveform converter 11b. The signal is subjected to the arithmetic processing including waveform superimposing, and is then recorded in the inspection result storage device 12 as a received waveform 35.

Next, measurements are performed with transmission and receiving functions switched between the guided wave sensors 3a, 3b. However, this switching is electrically performed by a signal from the inspection-result diagnostic device 13 to the trigger signal generator 5b. Processing in a step 104 shown in FIG. 16 is performed.

Figure 8:
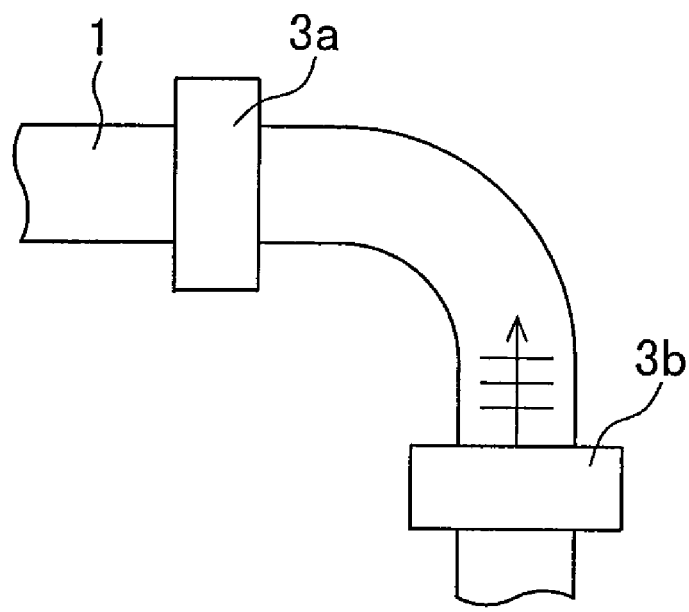
FIG. 8 is a diagram illustrating a third inspection process using a nondestructive inspection apparatus according to the second embodiment of the present invention.

As shown in FIG. 8, in response to a trigger signal from the trigger signal generator 5b, transmitted waves each having the same waveform are transmitted from the ultrasonic probe 21b through 25b according to the above-described operation. In this case, the phase and excitation amplitude are adjusted so that a guided wave mode which is suitable for inspection within a target range is excited. When a guided wave propagates from a straight piping portion at which the guided wave sensor 3b is disposed to a bending zone, a guided wave is broken up and passes through the bending zone.

This broken-up guided wave is received by each of the ultrasonic probes 21a through 25a of the guided wave sensor 3a. The received signal is then amplified by the receive amplifier 9 of each of the transmit-receive circuits 61a through 68a and the amplified signal is then transmitted to the digital signal converter 10. Next, the digital signal converter 10 converts the amplified signal into a digital signal, which is then transmitted to the received waveform converter 11a.

Next, processing in a step 105 shown in FIG. 16 is performed. The received waveform acquired by the received waveform converter 11a is transmitted to the arbitrary-waveform generator 7 as a waveform whose signal is time-reversed so that a signal being received last is transmitted first. In this case, the time-reversed waveform in the ultrasonic probe 21a is adapted to be received into the arbitrary-waveform generator 7 of the transmit-receive circuit 61a, and based on this configuration, the arbitrary-waveform generators of the other transmit-receive circuits are also set.

Figure 9:
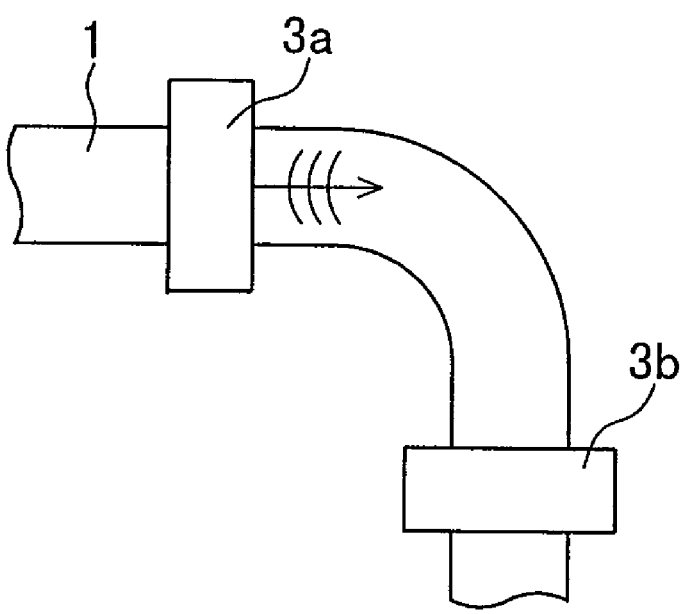
FIG. 9 is a diagram illustrating a fourth inspection process using a nondestructive inspection apparatus according to the second embodiment of the present invention.

Then, processing in a step 106 shown in FIG. 16 is performed. As shown in FIG. 9, in response to a trigger signal from the trigger signal generator 5a, a time-reversed wave, which has been inputted from each of the ultrasonic probes 21a through 25a to the arbitrary-waveform generator 7, is transmitted as an in-phase transmitted wave according to the above-described operation. As illustrated in FIG. 7, this process enables the broken-up-less wave control of a wave passing through the bending zone.

Inspection is carried out by use of this control wave. If a signal caused by bending or a defect such as wastage is present in a region within a range to be inspected, a reflected wave occurring at this point of time is received by the ultrasonic probes 21a through 25a. The received signal passes through each of the transmit-receive circuits 61a through 68a, and is then transmitted to the received waveform converter 11a. The signal is subjected to the arithmetic processing including waveform superimposing, and is then recorded in the inspection result storage device 12 as a received waveform 36.

Lastly, processing in a step 107 shown in FIG. 16 is performed. An identification method for identifying a defect will be described with reference to FIG. 10. The received waveform 35 received by the guided wave sensor 3b and the received waveform 36 received by the guided wave sensor 3a are output from the inspection result storage device 12 to the inspection-result diagnostic device 13. After that, the inspection-result diagnostic device 13 performs the undermentioned arithmetic operation. The result of the arithmetic operation is output to the display unit 14.

Figure 10:
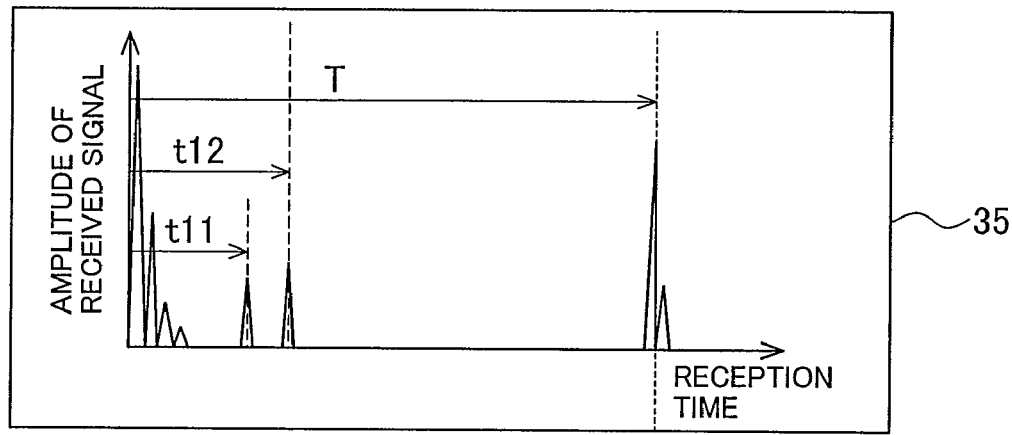
FIG. 10 shows charts each illustrating a fifth inspection process using a nondestructive inspection apparatus according to the second embodiment of the present invention.
Figure 10:
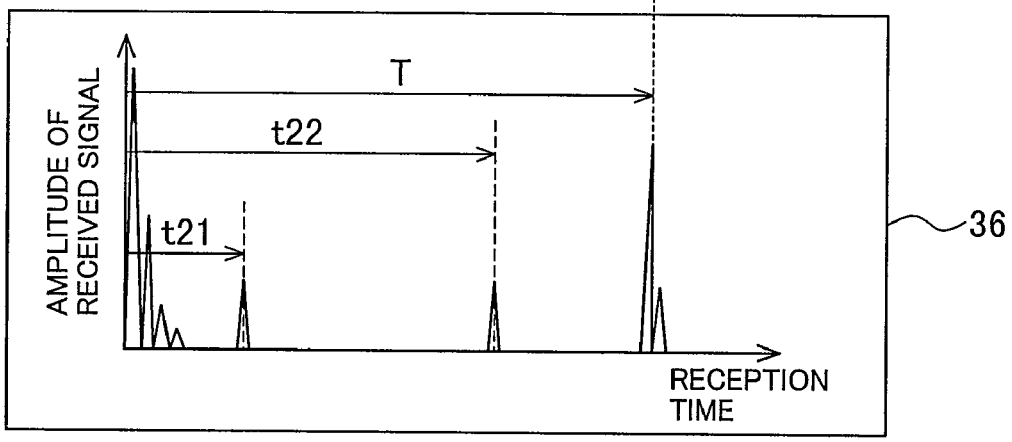
Figure 10:
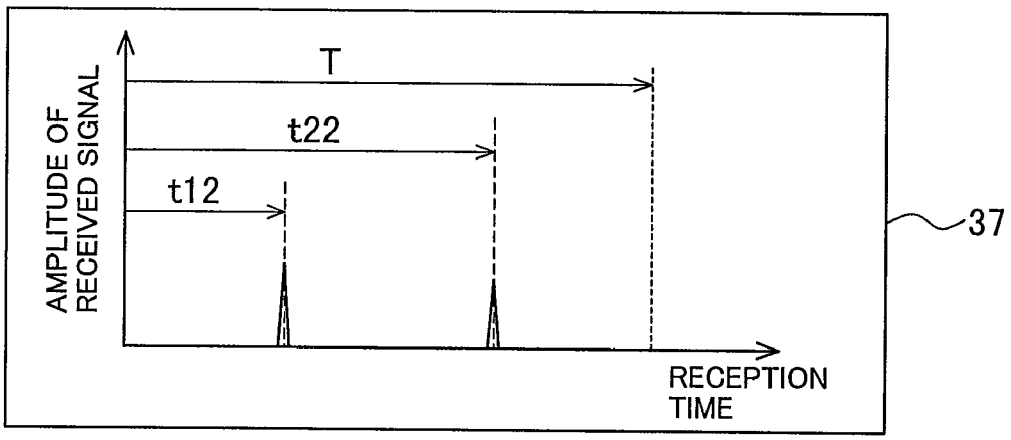

In the embodiment of the present invention, a case where guided wave sensors are disposed at positions, each of which is spaced away from the central part of a bending zone by the same distance, will be described. Incidentally, symbols shown in FIG. 10 are as follows: t11 and t21 denote the back-and-forth propagation time of a signal caused by a bending shape; t12 and t22 denote the back-and-forth propagation time of a signal caused by a defect; and T denotes the back-and-forth propagation time of a guided wave between the guided wave sensors 3a, 3b for a signal caused by bending.

If it is assumed that a signal is caused by a bending shape, it is judged that a bending zone has been symmetrically processed from the central part. Accordingly, the signal appears at a position whose distance from the guided wave sensor 3a is the same as that from the guided wave sensor 3b. In other words, the signal appears at a position at which the propagation time is the same. Therefore, equations 1 hold. As a result, the signal can be extracted as a nondefective signal.

$$t11=t21, t11+t21 \neq T \quad \text{(Equations 1)}$$

Therefore, on the basis of the equations 1, it is possible to determine a waveform 37 that is the difference between the received waveform 35 and the received waveform 36. Next, if it is assumed that the signal is caused by a defect, the sum of the distance from a defective portion to the guided wave sensor 3a and the distance from the defective portion to the guided wave sensor 3b is equivalent to the distance between the guided wave sensors 3a and 3b. Accordingly, the sum of the receiving time is calculated for all combinations of signal components that exceed a predetermined threshold value of the amplitude of the waveform 37. A signal which satisfies the relationship of an equation 2 can be identified as a defect.

$$t12+t22=T \quad \text{(Equation 2)}$$

However, a signal generated from the central part of the bending zone satisfies the equation 2 even if the signal is caused by a bending shape. In this case, inspection is performed by use of a guided wave whose transmit frequency has been changed, or a guided wave whose phase and excitation amplitude has been adjusted. Then, a signal is reevaluated according to the steps described with reference to FIGS. 6 through 10. Here, if a significant signal satisfying the equation 2 is obtained, it is desirable to evaluate the soundness by auxiliary means such as thickness measurement using an ultrasonic thickness gauge.

Figure 18:
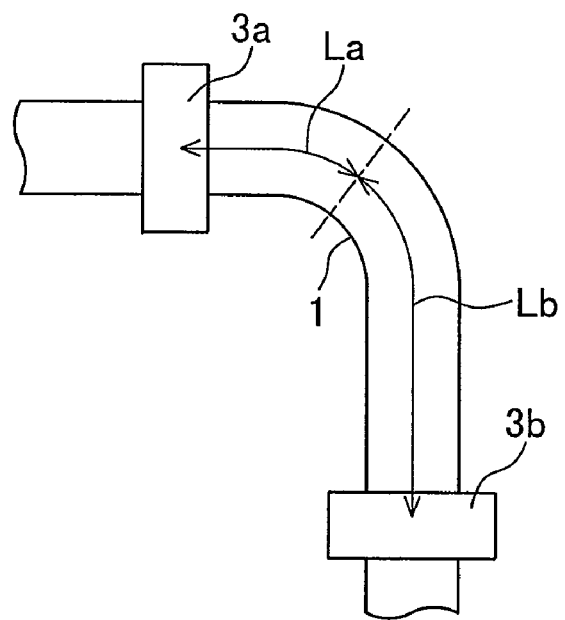
FIG. 18 is a diagram illustrating the time starting point adjustment based on the difference in placement position between guided wave sensors according to the second embodiment of the present invention.

In the embodiment of the present invention, a case where both of the guided wave sensors are disposed at positions, each of which is spaced away from the central part of the bending zone by the same distance, was described. However, even if both of the guided wave sensors are disposed at positions, each of which is spaced away from the central part of the bending zone by a different distance, if a time starting point is shifted according to the distance, it is possible to carry out the defect identification according to the present invention. Therefore, this case also falls within the category of the present invention. For example, as shown in FIG. 18, on the assumptions that the distance from the center of the bending zone to the center of the guided wave sensor 3a is La, and that the distance from the center of the bending zone to the center of the guided wave sensor 3b is Lb, and that the sound velocity of a guided wave propagating through the piping is V, the moving time T of a time starting point is expressed by an equation 3. If the guided wave sensors are placed at positions shown in FIG. 18, the processing described in FIG. 10 becomes effective by subtracting only T from the receiving time of a received waveform of the guided wave sensor 3b.

$$T=(Lb-La)/V \quad \text{(Equation 3)}$$

Although the steps using the time reversing were described as above, there is a case where a waveform is not broken-up depending on the transmit frequency and a bending shape, and therefore, it is not necessary to use the waveform control based on the time reversing. In this case, because it is not necessary to use the waveform control based on a time-reversing wave, the processing relating to the generation of the time-reversing wave can also be excluded.

Figure 11:
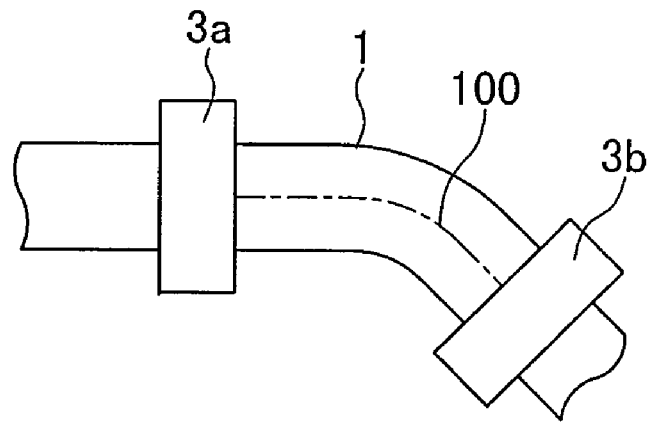
FIG. 11 is a diagram illustrating an example 1 of a piping shape that can be handled by the second embodiment of the present invention.
Figure 12:
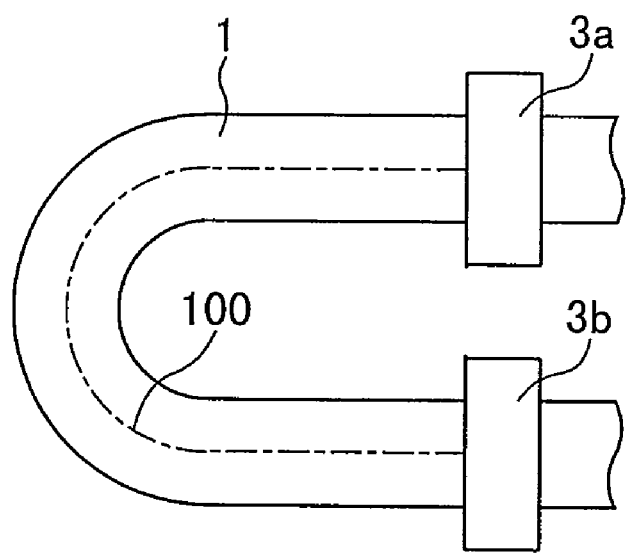
FIG. 12 is a diagram illustrating an example 2 of a piping shape that can be handled by the second embodiment of the present invention.
Figure 13:
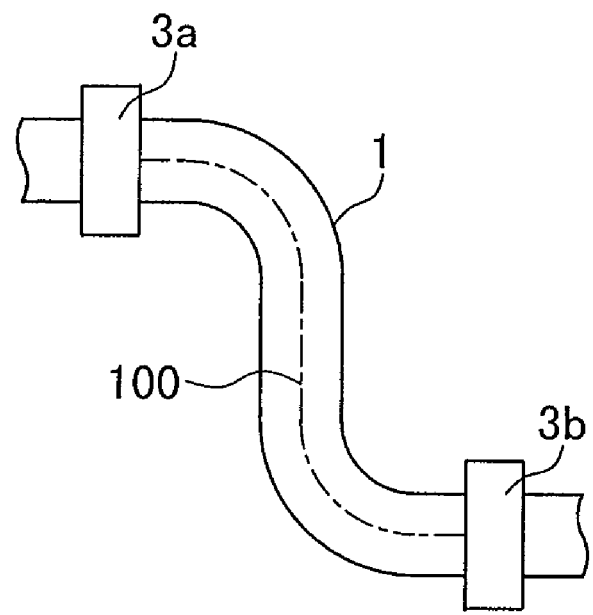
FIG. 13 is a diagram illustrating an example 3 of a piping shape that can be handled by the second embodiment of the present invention.
Figure 14:
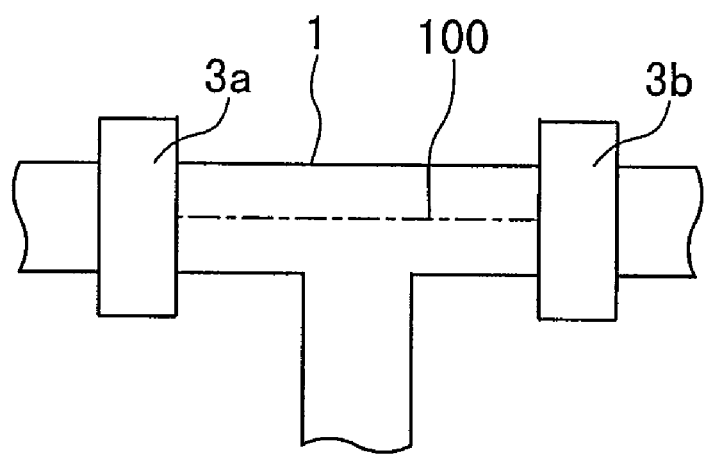
FIG. 14 is a diagram illustrating an example 4 of a piping shape that can be handled by the second embodiment of the present invention.
Figure 15:
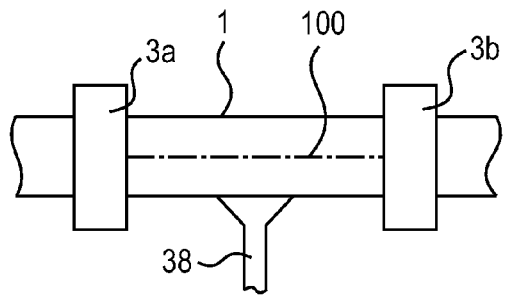
FIG. 15 is a diagram illustrating an example 5 of a piping shape that can be handled by the second embodiment of the present invention.

In addition, according to the embodiment of the present invention, the diagram illustrating the curved piping whose bending angle is 90° was made. However, even in a straight piping, a bending zone as shown in FIGS. 11 through 13, a T-shaped branch piping as shown in FIG. 14, and piping equipped with a support structure 38 as shown in FIG. 15, piping inspection of piping whose range to be inspected includes a symmetrical shape also fall within the category of the present invention.

As described in the embodiment of the present invention, according to the defect identification method in which two received signals are compared in the inspection using a guided wave so as to identify a defect from the significant difference that exceeds a predetermined threshold value of the amplitude, it is possible to detect a defect by the inspection using a guided wave even in a bending zone whose thickness is conventionally obliged to be measured by an ultrasonic thickness gauge. This makes it possible to complete the inspection in a shorter period of time than that in the thickness measurement using the conventional ultrasonic thickness gauge. In particular, in a case where a caliber is large, a guided wave sensor suitable for the large caliber may be selected so that the inspection by the totally same system is possible. Therefore, the effects of reducing the inspection time are very large in comparison with the method using the ultrasonic thickness gauge which has an enormous number of thickness measuring points.

As described in each of the above embodiments, the description includes a number of technical points, which will be described as below. To be more specific, a first technical point relates to a nondestructive inspection apparatus including: generation means for exciting an elastic wave into a piping to propagate a guided wave, the generation means being disposed on an outer surface of the piping; receiving means for receiving the guided wave propagating through the piping, the receiving means being disposed on the outer surface of the piping; recording means for converting the guided wave received by the receiving means into a digital signal so that the digital signal is handled as a received wave; storage means for storing the received wave that has been acquired by the recording means; and diagnosis means that is capable of carrying out arithmetic processing for the signal obtained by reproducing the received wave which has been stored in the storage means, and for a signal of the received wave which has been recorded by the recording means.

A second technical point relates to a nondestructive inspection apparatus including: generation means for exciting an elastic wave into a piping to propagate a guided wave, the generation means being disposed on an outer surface of the piping; receiving means for receiving the guided wave propagating through the piping, the receiving means being disposed on the outer surface of the piping; recording means for converting the guided wave received by the receiving means into a digital signal so that the digital signal is handled as a received wave; calculation means for calculating the behavior of the guided wave propagating through the piping on the basis of characteristics of the piping and information about a transmission signal of propagation means; storage means for storing a calculated waveform that has been acquired by the calculation means; and diagnosis means that is capable of carrying out arithmetic processing for the signal obtained by reproducing the calculated waveform which has been stored in the storage means, and for a signal of the received wave which has been recorded by the recording means.

A third technical point relates to the nondestructive inspection apparatus according to the first or second technical point, wherein: on the basis of the difference in receiving time between a read signal and a received signal, it is possible to detect a defect that has occurred in the piping.

A fourth technical point relates to a nondestructive inspection apparatus including: a pair of means that is capable of exciting an elastic wave into a piping to propagate a guided wave, and that is capable of receiving the guided wave propagating through the piping, the pair of means being disposed on an outer surface of the piping; recording means for converting the guided wave received by the receiving means into a digital signal so that the digital signal is handled as a received wave; storage means for storing the received wave that has been acquired by the recording means; and means for transmitting, from the pair of means, a waveform as a transmission signal, the waveform being obtained by time-reversing a waveform reproduced from the storage means; and diagnosis means that is capable of carrying out arithmetic processing for the signal obtained by reproducing the received wave which has been stored in the storage means, and for a signal of the received wave which has been recorded by the recording means.

A fifth technical point relates to a nondestructive inspection method including the steps of: disposing a pair of means A and B, each of which is capable of generating and receiving a guided wave, in such a manner that a range of piping to be inspected is put between the pair of means A, B; receiving the guided wave, which has been generated by the one means A, by the other means B, and transmitting the guided wave, which has been subjected to waveform control by time-reversing on the basis of the received wave, to the range of piping to be inspected by the means B, and then handling a waveform received by the means B as a received signal 1; receiving, by the means A, the guided wave that has been generated by the means B, and transmitting the guided wave, which has been subjected to waveform control by time-reversing on the basis of the received wave, to the range of piping to be inspected by the means A, and then handling a waveform received by the means A as a received signal 2; and identifying a signal caused by a defect by calculating the sum and difference of the receiving time between the received signal 1 and the received signal 2.

Any of the above-described technical points makes it possible to detect, by the inspection using a guided wave, a defect in a bending zone whose thickness is conventionally obliged to be measured by an ultrasonic thickness gauge. As a result, it becomes possible to complete the inspection in a shorter period of time than that in the thickness measurement using the conventional ultrasonic thickness gauge. In particular, in a case where a caliber is large, a guided wave sensor suitable for the large caliber may be selected so that the inspection by the totally same system is possible. Therefore, the effects of reducing the inspection time are very large in comparison with the method using the ultrasonic thickness gauge which has an enormous number of thickness measuring points.

The present invention is applicable to nondestructive inspection that uses a guided wave to inspect whether or not piping has a defect including wastage.

What is claimed is:

1. A nondestructive inspection apparatus comprising:
a pair of guided wave inspection devices connected to a pair of guided wave sensors which are disposed on an outer surface of a piping, each of said devices exciting an elastic wave into the piping to propagate a guided wave, each of said devices receiving the guided wave propagating through the piping;
an inspection-result storage device for storing the guided wave received by said guided wave inspection device as a digitized signal of the received wave; and
an inspection-result diagnostic device for, by taking an added value or differential value of back-and-forth propagation time of receive wave which exceeds a predetermined threshold value in a signal of each received wave acquired by transmitting a guided wave by use of said pair of guided wave inspection devices into the piping by use of said pair of guided wave inspection devices, performing arithmetic processing of judging whether or not a signal associated with a defect exists.

2. The nondestructive inspection apparatus according to claim 1,
which further includes means for transmitting, as a transmission signal, a waveform obtained by time-reversing a received waveform from said pair of guided wave inspection devices.

3. The nondestructive inspection apparatus according to claim 1,
wherein said inspection-result diagnostic device identifies as a non-defective signal, in the received wave which exceeds a predetermined threshold value in the signal of each received wave obtained through said pair of guided wave inspection devices, and when back and forth propagation time of a received wave form received by one guided wave sensor is set to t11, back and forth propagation time of the received wave form received by the other guided wave sensor is set to t21, and back and forth propagation time of the guided wave between said pair of guided wave sensors is set to T, and when relations of t11=t12 and t11+t12≠T are realized.

4. The nondestructive inspection apparatus according to claim 1,
wherein said inspection-result diagnostic device identifies as a defective signal, in the received wave which exceeds a predetermined threshold value in the signal of each received wave obtained through said pair of guided wave inspection devices, and when back and forth propagation time of a received wave form received by one guided wave sensor is set to t11, back and forth propagation time of the received wave form received by other guided wave sensor is set to t21, and back and forth propagation time of the guided wave between said pair of guided wave sensors is set to T, and when relations of t11=t12 and t11+t12=T are realized.

5. The nondestructive inspection apparatus according to claim 1,
wherein said inspection-result diagnostic device identifies the existence of a signal accompanying a defect, when said pair of guided wave sensors are disposed at different positions, each of which is spaced away from the central part of the bending zone of the piping by a different distance, and when a distance from the central part of the bending zone of the piping to one guided wave sensor is set to La, and when a distance from the central part of the bending zone of the piping to other guided wave sensor is set to Lb, and when acoustic velocity of the guided wave which spreads a siphon is set to V, and only T is deducted from the time of the received wave of the guided wave sensor of another side by setting travel time T of a time starting point to (Lb−La)/V.

6. A nondestructive inspection method comprising the steps of:
disposing a pair of means A and B, each of which generates and receives a guided wave, in such a manner that a range of piping to be inspected is placed between the pair of means A, B;
receiving the guided wave generated by one means A by the other means B, allowing the means B to transmit the guided wave which has been subjected to waveform control by time-reversing on the basis of the received wave to the range of piping to be inspected, and handling a waveform received by the means B as a received signal 1;
receiving a guided wave generated by the means B by the means A, allowing the means A to transmit the guided wave which has been subjected to waveform control by time-reversing on the basis of the received wave to the range of piping to be inspected, and handling a waveform received by the means A as a received signal 2; and
identifying a signal derived from a defect by calculating the sum or difference of back-and-forth propagation time of receive wave which exceeds a predetermined threshold value in the received signal 1 and the received signal 2.

7. A nondestructive inspection method comprising the steps of:
disposing a pair of means A and B, each of which is capable of generating and receiving a guided wave, in such a manner that a range of piping to be inspected is put between the pair of means A and B;
receiving the guided wave generated b one means A by the other means B, and handling a waveform received by the means B as received signal 1;
receiving a guided wave generated by the means B and by the means A, and handling a waveform received by the means A as a received signal 2; and
identifying a signal derived from a defect by calculating the sum or difference of back-and-forth propagation time of receive wave which exceeds a predetermined threshold value in the received signal 1 and the received signal 2.

8. The nondestructive inspection method according to claim 7,
wherein said inspection-result diagnostic device identifies as a non-defective signal, when back and forth propagation time of a received wave form received by one of a pair of guided wave sensors is set to t11, back and forth propagation time of the received wave form received by the other of the pair of guided wave sensors is set to t21, and back and forth propagation time of the guided wave between said pair of guided wave sensors is set to T, and when relations of t11=t12 and t11+t12≠T are realized.

9. The non-destructive inspection method according to claim 7,
wherein said inspection-result diagnostic device identifies as a defective signal, when back and forth propagation time of a received wave form received by one of a pair of guided wave sensors is set to t11, back and forth propagation time of the received wave form received by the other of the pair of guided wave sensors is set to t21, and back and forth propagation time of the guided wave between said pair of guided wave sensors is set to T, and when relations of t11=t12 and t11+t12=T are realized.

10. The nondestructive inspection method according to claim 7,
wherein said inspection-result diagnostic device identifies the existence of the signal accompanying a defect, when a distance from the central part of the bending zone of the piping to one of a pair of guided wave sensors is set to La, when a distance from the central part of the bending zone of the piping to the other of a pair of guided wave sensor is set to Lb, and when acoustic velocity of the guided wave which spreads a siphon is set to V, and only T is deducted from the time of the received wave of the guided wave sensor of another side by setting travel time T of a time starting point to (Lb−La)/V.

* * * * *